(12) United States Patent
Tramontina et al.

(10) Patent No.: US 12,129,104 B2
(45) Date of Patent: Oct. 29, 2024

(54) FACEMASK DISPENSER

(71) Applicant: Ansell Healthcare Products LLC, Iselin, NJ (US)

(72) Inventors: Paul F. Tramontina, Harleysville, PA (US); Randall W. LeCates, Monroeville, NJ (US)

(73) Assignee: Ansell Healthcare Products LLC, Iselin, NJ (US)

( * ) Notice: Subject to any disclaimer, the term of this patent is extended or adjusted under 35 U.S.C. 154(b) by 0 days.

(21) Appl. No.: 18/257,124

(22) PCT Filed: Sep. 17, 2021

(86) PCT No.: PCT/US2021/050840
§ 371 (c)(1),
(2) Date: Jun. 13, 2023

(87) PCT Pub. No.: WO2023/043451
PCT Pub. Date: Mar. 23, 2023

(65) Prior Publication Data
US 2024/0025628 A1   Jan. 25, 2024

(51) Int. Cl.
*B65D 83/08* (2006.01)
(52) U.S. Cl.
CPC .................. *B65D 83/0852* (2013.01)
(58) Field of Classification Search
CPC ............ B65D 83/0811; B65D 83/0852; B65D 83/0894; B65H 3/56
See application file for complete search history.

(56) References Cited

U.S. PATENT DOCUMENTS

| | | |
|---|---|---|
| 2,588,152 A | 3/1952 | Newman |
| 2,794,282 A * | 6/1957 | Sherman ............... B42F 17/346 40/389 |
| 3,094,323 A | 6/1963 | Catania |
| 4,071,165 A | 1/1978 | Leopoldi |
| 4,269,315 A | 5/1981 | Boyce |

(Continued)

FOREIGN PATENT DOCUMENTS

DE    2729572 A1    1/1979

OTHER PUBLICATIONS

PCT Search Report Corresponding to Application No. PCT/US2021/050840 on Jan. 17, 2022.

(Continued)

*Primary Examiner* — Gene O Crawford
*Assistant Examiner* — Kelvin L Randall, Jr.
(74) *Attorney, Agent, or Firm* — Moser Taboada (57) ABSTRACT

A dispenser for dispensing a facemask is provided. The dispenser includes a housing having an interior volume so as to retain one or more facemasks having a metal strip disposed thereon or therein and a cover assembly forming at least a portion of the housing, the cover assembly including an outer surface forming a portion of an exterior of the dispenser and an inner surface facing the interior volume. An arm is disposed on the inner surface of the cover assembly, the arm including a first end having a magnetic device disposed thereon, wherein the magnetic device is configured to lift one or more facemasks to a dispensing position when the cover assembly is moved to an opened position.

19 Claims, 8 Drawing Sheets

(56) References Cited

U.S. PATENT DOCUMENTS

| | | | | |
|---|---|---|---|---|
| 4,986,417 | A * | 1/1991 | Hsu | B43M 99/009 |
| | | | | 206/214 |
| 5,803,075 | A * | 9/1998 | Yavitz | A41D 13/1115 |
| | | | | 128/206.28 |
| 6,202,889 | B1 * | 3/2001 | Veith | B65D 83/0817 |
| | | | | 221/63 |
| 7,661,555 | B1 | 2/2010 | Evans et al. | |
| 9,381,068 | B2 | 7/2016 | Konishi | |
| 9,414,721 | B2 | 8/2016 | Marin-Quintero et al. | |
| 9,914,599 | B2 * | 3/2018 | Namuduri | B65G 59/04 |
| 2004/0099677 | A1 * | 5/2004 | Harris | B65D 83/0805 |
| | | | | 221/33 |
| 2006/0266758 | A1 * | 11/2006 | Lewis | B65H 1/04 |
| | | | | 221/33 |
| 2006/0266759 | A1 * | 11/2006 | Tramontina | B65D 83/0894 |
| | | | | 221/33 |
| 2009/0302048 | A1 | 12/2009 | Nobilet et al. | |
| 2011/0204078 | A1 * | 8/2011 | Mulhem | B60N 3/101 |
| | | | | 221/45 |
| 2014/0367401 | A1 * | 12/2014 | Stralin | A47K 10/38 |
| | | | | 221/6 |
| 2015/0191299 | A1 | 7/2015 | Tsuei | |
| 2019/0352084 | A1 * | 11/2019 | Modha | B65D 5/724 |
| 2020/0115143 | A1 * | 4/2020 | Rutan | B65D 83/0805 |
| 2021/0361125 | A1 * | 11/2021 | Racioppi | A47K 5/1202 |
| 2022/0193294 | A1 * | 6/2022 | Novelo Ascencio | |
| | | | | A61L 2/0088 |

OTHER PUBLICATIONS

ELMECO, Earloop Face Mask Holder (Magnet Mount), http://www.elmecoengineering.com/products/earloop-face-mask-holder-magnet-mount.

Simplicity Gifts Singapore, Hard Case Face Mask Holder, https://simplicitygifts.com.sg/product/hard-case-face-mask-holder/.

* cited by examiner

FACEMASK DISPENSER

RELATED APPLICATIONS

The present application is the national stage entry of International Patent Application No. PCT/US2021/050840 having a filing date of Sep. 17, 2021, which is incorporated herein in its entirety by reference thereto.

BACKGROUND

Disposable face masks have been manufactured for many years. In the medical field, early masks were designed to protect patients from pathogens contained in the exhaled air of health care personnel. In recent years, it has likewise become important to protect not only medical professionals but also the general public from airborne pathogens emitted by individuals that may have been exposed to certain pathogens. For example, due to transmission of Covid-19, facemasks are being worn more than ever. Additionally, many commercial establishments, such as doctor's offices, grocery stores, gas stations, etc., are now providing disposable masks for patrons to wear while they are indoors. However, currently facemasks are bulk packaged typically in some type of paperboard container that exposes the masks contained therein to the ambient environment and, thus, can compromise the sterility of the masks. Furthermore, as user's reach into containers to access a facemask they can inadvertently touch other facemasks therein, thus contaminating other facemasks stored in the container.

Accordingly, there is a need for a dispensing facemasks in a hygienic manner such that masks remaining in the dispenser are not contaminated by a user's hands or the ambient environment.

SUMMARY

In general, the present disclosure is directed to a dispenser for dispensing a facemask. The dispenser includes a housing having an interior volume so as to retain one or more facemasks having a metal strip disposed thereon or therein and a cover assembly forming at least a portion of the housing, the cover assembly including an outer surface forming a portion of an exterior of the dispenser and an inner surface facing the interior volume. An arm is disposed on the inner surface of the cover assembly, the arm including a first end having a magnetic device disposed thereon, wherein the magnetic device is configured to lift one or more facemasks to a dispensing position when the cover assembly is moved to an opened position.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

As used herein, the terms "first", "second", and "third" may be used interchangeably to distinguish one component from another and are not intended to signify location or importance of the individual components.

The terms "coupled", "fixed," "attached to," and the like refer to both direct coupling, fixing, or attaching, as well as indirect coupling, fixing, or attaching through one or more intermediate components or features, unless otherwise specified herein.

The terms "communicate," "communicating," "communicative," and the like refer to both direct communication as well as indirect communication such as through a memory system or another intermediary system.

The singular forms "a", "an", and "the" include plural references unless the context clearly dictates otherwise.

Approximating language, as used herein throughout the specification and claims, is applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 1, 2, 4, 10, 15, or 20 percent margin. These approximating margins may apply to a single value, either or both endpoints defining numerical ranges, and/or the margin for ranges between endpoints.

The embodiments including dispenser and methods of the present disclosure, including components thereof, can comprise, consist of, or consist essentially of the essential elements and limitations of the embodiments described herein, as well as any additional or optional components or limitations described herein or otherwise useful.

Facemasks, especially disposable facemasks, often are bulk packaged in a paperboard container with an opening so that a user can access and pull one or more facemasks from the container. Additionally, bulk packaged facemasks can be mounted on surfaces, such as walls, so that users can easily access masks stored therein. While disposable facemasks are increasingly being utilized by the general public, it remains that often times users can contaminate one or more masks while attempting to remove a mask from a paperboard container.

Accordingly, the present disclosure is generally directed to a dispenser for dispensing a disposable product. The dispenser includes a housing having an interior volume so as to retain one or more facemasks having a metal strip disposed thereon or therein and a cover assembly forming at least a portion of the housing, the cover assembly including an outer surface forming a portion of an exterior of the dispenser and an inner surface facing the interior volume. An arm is disposed on the inner surface of the cover assembly. The arm includes a first end having a magnetic device disposed thereon. The magnetic device is configured to lift one or more facemasks to a dispensing position when the cover assembly is opened. Optionally, the dispenser can include a cartridge disposed in the interior volume of the dispenser that is configured to hold the facemasks in a stacked position. The cartridge can include an opening having a hygienic film disposed thereon. The hygienic film can include a slit through which one or more facemasks can be removed.

The dispenser according to example embodiments of the present disclosure can provide numerous benefits. For example, use of the dispenser arm to remove facemasks from the stack ensures that facemasks remaining in the dispenser are not unduly contaminated. Furthermore, use of the cartridge including the hygienic film can further protect the sterility of remaining facemasks in the dispenser.

Figure 1:
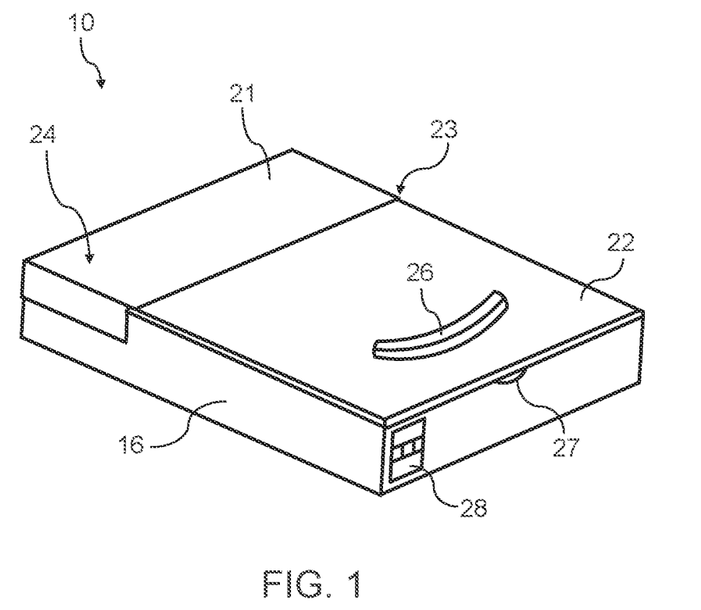
FIG. 1 illustrates a perspective view of a dispenser with the cover assembly in a closed position according to example embodiments of the present disclosure.

FIG. 1 illustrates an example embodiment of a dispenser 10 for dispensing facemasks in accordance with embodiments of the present disclosure. The dispenser 10, as shown, is configured for dispensing facemasks, such as disposable facemasks. Features of the dispenser disclosed herein may be applicable to other types of dispenser for dispensing other consumable products. Furthermore, the dispensers disclosed herein can include counter mounted product dispensers, wall-mounted product dispensers, including dispensers mounted to walls, and/or stand-alone product dispensers.

Figure 2:
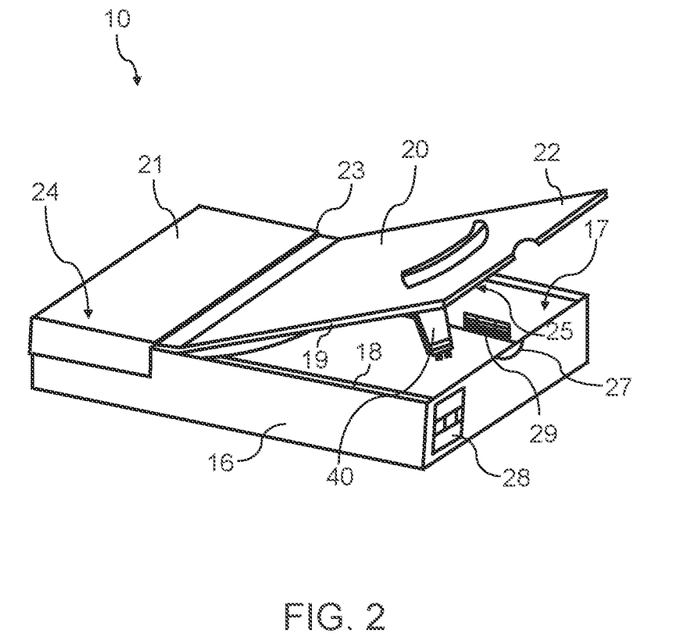
FIG. 2 illustrates a perspective view of a dispenser with the cover assembly in an open position according to example embodiments of the present disclosure.
Figure 3:
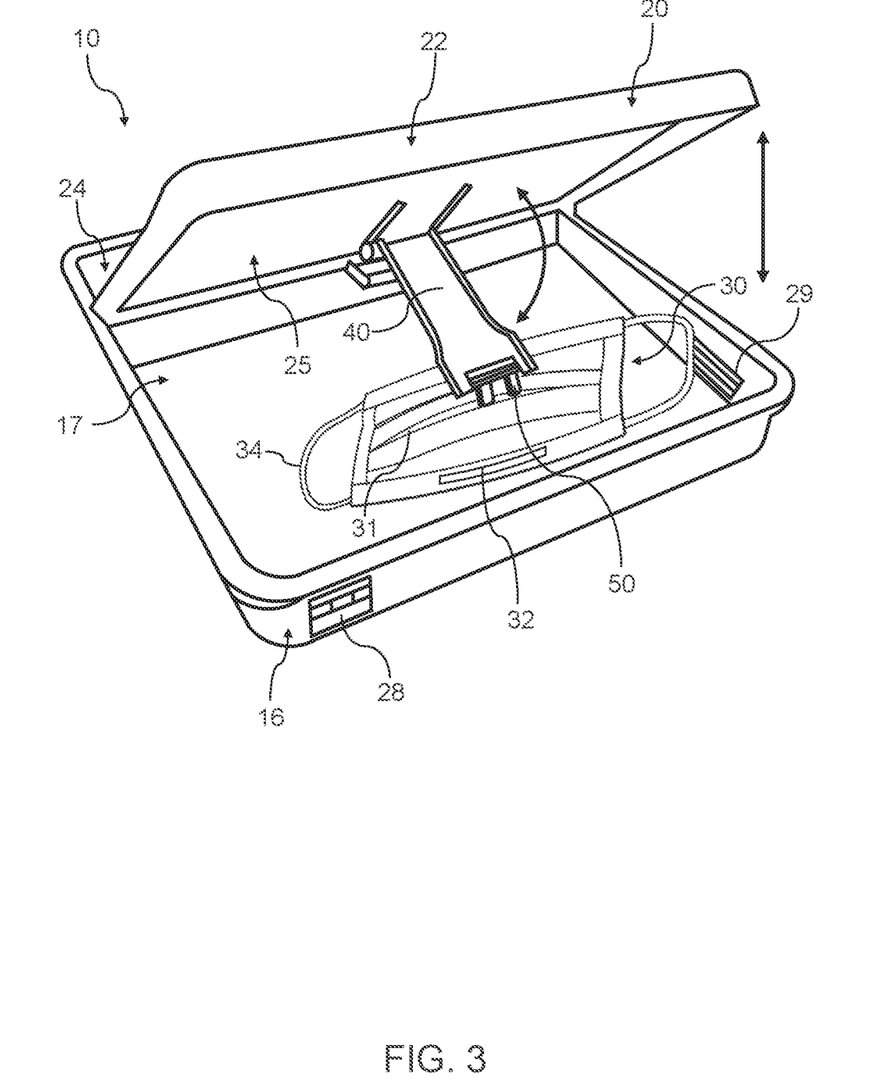
FIG. 3 illustrates a perspective view of a dispenser with the cover assembly in an open position according to example embodiments of the present disclosure.

As shown in FIGS. 1-3, the dispenser 10 includes a housing 16 having a interior volume 17 that is designed to house one or more facemasks. The housing 16 may be formed of any suitable materials. The dispenser 10 includes a cover assembly 20. As shown in FIG. 2, the cover assembly 20 is shown in an open position. In certain embodiments, the cover assembly 20 can define one or more of the sidewalls of the dispenser 10. In other embodiments, however, the cover assembly 20 can form at least a portion, but not substantially all, of the sidewalls of the dispenser 10. In other embodiments, however, the cover assembly 20 does not form any portion of the sidewalls of the dispenser. The cover assembly 20 can be coupled to the housing 16 via any suitable mechanism. For example, the cover assembly can be pivotally coupled to the housing 16. For example, one or more hinges can be used to pivotally couple the cover assembly 20 to the housing 16. Any conventional pivotal attaching mechanism may be used in this regard. For example, in certain embodiments, a simple rotatable rod is provided and retained by rod holders. It should be appreciated that any number of conventional pivotal arrangements are known by those skilled in the art that may be utilized to pivotally mount the cover assembly 20 to the housing 16. In other embodiments, the cover assembly 20 can be completely removable or detachable from the housing 16.

The cover assembly 20 and housing 16 can be configured to fit together in a tongue and groove arrangement. For example, as shown in FIG. 2, the housing 16 can include a groove 18 running along at least a portion and/or the entire perimeter of the housing 16. The groove 18 can be shaped in such as manner so as to received the perimeter 19 of the cover assembly 20. Thus, when the cover assembly 20 is placed in a closed position with respect to the housing 16, the cover assembly 20 and housing 16 have a flush fit such that no contaminants are capable of entering the interior volume 17 of the housing. Furthermore, in certain embodiments, the cover assembly 20 can include a flange or other continuous tab disposed on the perimeter 19 of the cover assembly 20 for facilitating fit between the housing 16 and the cover assembly 20. Additionally, to ensure a proper seal between the cover assembly 20 and the housing 16, either the perimeter of the housing 16 or the cover assembly 20 can be outfitted with a gasket (not shown). The gasket can be formed from any suitable elastomeric material. The gasket can further ensure a proper seal between the cover assembly 20 and the housing 16, when the cover assembly is in a closed position.

In certain embodiments, the cover assembly 20 includes a back portion 21 and a front portion 22 that are generally delineated by a pivot point 23. For example, as shown, the back portion 21 can be securely coupled to the housing 16, such that the back portion 21 of the cover assembly 20 remains coupled to the housing 16 when the front portion 22 is lifted to an open position. The pivot point 23 can include any suitable hinge, including a living hinge, that is capable of allowing the front portion 22 of the cover assembly 20 to open such that contents within the housing 16 can be accessed by a user. The cover assembly 20 further includes an outer surface 24 and an inner surface 25. The outer surface 24 forms a portion of an exterior of the dispenser 10 while the inner surface 25 faces the interior volume 17 of the dispenser, especially when the cover assembly 20 is in a closed position. An arm 40 is disposed on the inner surface 25 of the cover assembly 20. The arm 40 is configured to remove one or more facemask from a stack within the interior volume 17 to a dispensing position, as will be discussed further hereinbelow.

Additionally, the housing 16 and/or cover assembly 20 can be outfitted with additional features to facilitate opening of the dispenser 10. For example, optionally, a tab 26 can be disposed on the outer surface 25 of the cover assembly 20. The tab 26 is disposed such that a user can grip the tab 26 to facilitate opening of the front portion 22 of the cover assembly 20 to reveal the contents of the dispenser 10. Additionally, a groove 27 can be provided in either the cover assembly 20 or the housing 16 in order to facilitate opening of the dispenser 10.

Figure 4:
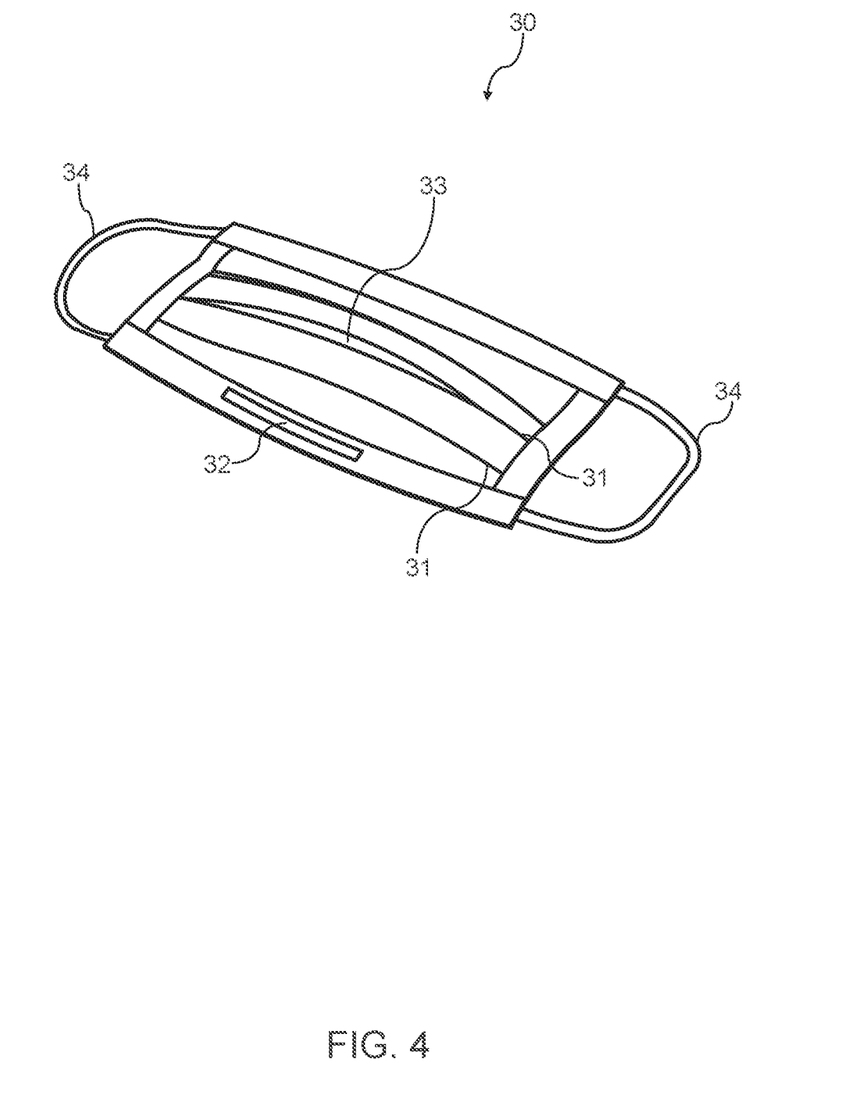
FIG. 4 illustrates a perspective view of a facemask for use with the dispenser according to example embodiments of the present disclosure.

The housing 16 includes an interior volume 17 configured so as to retain one or more facemasks 30 having a metal strip 32 thereon. FIG. 3 illustrates an embodiments of a dispenser 10 having one or more facemasks 30 disposed therein, while FIG. 4 illustrates an example of a suitable facemask 30 according to embodiments of the present disclosure. As shown, the facemask 30 may have a rectangular shape with one or more pleats 31. While a rectangular facemask is shown, the disclosure is not so limited. Indeed, any shape of facemask can be used in accordance with the dispenser provided herein. For example, in certain embodiments the facemask can be ovular or circular in shape. In other embodiments, the face mask can have an irregular shape that corresponds to curvatures of the face. The facemask 30 can be packaged in a flat configuration such that multiple facemasks can be arranged in a stacked configuration. When ready to wear, the pleats 31 can be partially opened or expanded so that the wearer can comfortable fit the facemask 30 directly to their face.

The facemask 30 can be formed from any suitable material. For example, the facemask 30 may be formed from filtration materials which may be rigid, pre-molded, or flexible. In one embodiment, the facemask 30 may be formed from a flexible fabric laminate of layers of a nonwoven material. The flexible fabric laminate is sufficiently porous to preform as a suitable contaminate barrier while permitting the wearer to easily breath therethrough. It has been found that nonwoven webs formed from polyolefin-based fibers are particularly well-suited for use as a filtration material in the present invention. Examples of such nonwoven webs are the polypropylene nonwovens produced by the Assignee of record, Kimberly-Clark Corporation. One such multiple-layered nonwoven web, a spunbond, meltblown, spunbond (SMS) nonwoven web, is produced by Kimberly-Clark Corporation. This spunbond, meltblown, spunbond web may be made from three separate layers which are laminated to one another. Such a method of making this laminated web is described in commonly assigned U.S. Pat. No. 4,041,203 to Brock et al which is incorporated herein in its entirety by reference. Alternatively, the spunbond, meltblown, spunbond web may be made by first forming a spunbond-meltblown laminate. The spunbond-meltblown laminate is formed by applying a layer of meltblown on to a layer of spunbond. The second layer of spunbond is then applied to the meltblown side of the previously formed spunbond-meltblown laminate. Generally, the two outer layers provide the nonwoven web with strength while the inner layer provides barrier properties. Various techniques may be used to increase the rigidity of the facemask 30. In some embodiments, the facemask 30 may be thermally molded or heat set to increase stiffness. In other embodiments, binder chemicals may be added to the materials prior to formation of the facemask 30.

The facemask 30 can include a metal strip 32 disposed therein. The metal strip 32 is located along one side of the facemask 30 and can be manipulated so that the mask can conform to the nose bridge of the wearer. For example, when in a packaged and stored position, the metal strip 32 is positioned to lie flat for easier stacking and storage of multiple facemasks 30. However, upon use, the wearer can bend or form the metal strip into a rigid shape in order to impart additional shape into the facemask 30 so that the facemask 30 is more secure and comfortable to wear. The metal strip 32 can include any suitable metal material capable of forming an attraction with a magnet. For example, in some embodiments, the metal material can include a ferromagnetic metal. Ferromagnetic metals include those that are strongly attracted to magnetic fields and are generally able to retain their magnetic properties after the magnet is removed. Such materials include iron, nickel, cobalt, gadolinium, dysprosium, and alloys thereof. In certain embodiments, the metal material can include paramagnetic materials. Paramagnetic materials include those that are more weakly attracted to magnets and do not retain magnetic properties when the magnet is removed. Such materials, include coper, aluminum, platinum, and alloys thereof. In certain embodiments, the metal material includes aluminum. The facemask 30 is secured to the user's face by one or more ear loops 34 that are disposed on one or more sides of the facemask 30. For example, at least two ear loops 34 can be disposed on each side of the facemask 30. The ear loops 34 can be formed from an elastomeric material such that they can be pulled around the wearer's ears to secure the facemask 30 to the user's face.

As shown in FIG. 3, the facemasks 30 can be stacked within the interior volume 17 such that the open end 33 of the pleats 31 are oriented towards the front of the dispenser 10. As will be discussed further hereinbelow, such an orientation can facilitate removal of the top facemask 30 from the stack by the arm 40. For example, disposition of the facemasks 30 with the open end 33 of the pleats 31 oriented towards the front of the dispenser 10, reduces frictional forces as the magnetic device 50 makes contact with and moves across the top facemask 30 towards the metal strip 32. Additionally, the facemasks 30 can be stacked within the interior volume 17 such that the metal strips 32 are oriented towards the front of the dispenser 10. Again, as will be discussed further, placement of the metal strips 32 in such a location in the stack can facilitate removal of the top facemask 30 from the stack.

Figure 5:
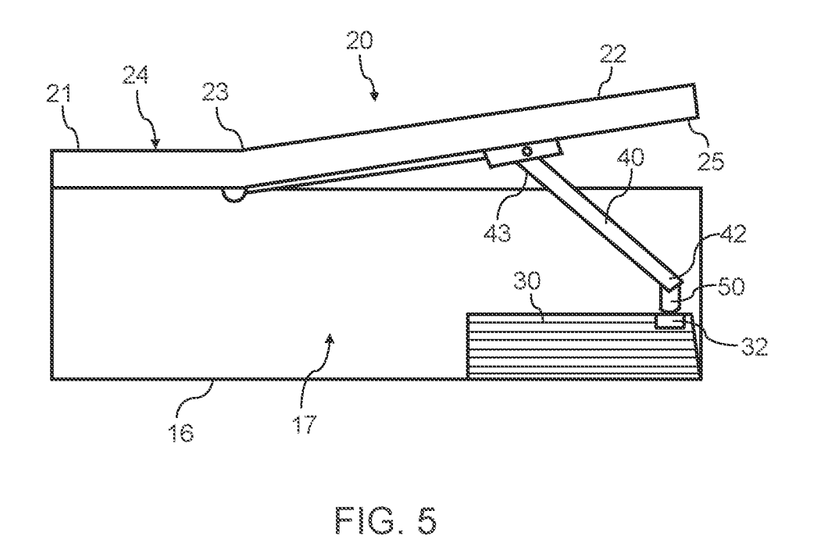
FIG. 5 illustrates a cross sectional view of a dispenser according to example embodiments of the present disclosure.
Figure 6:
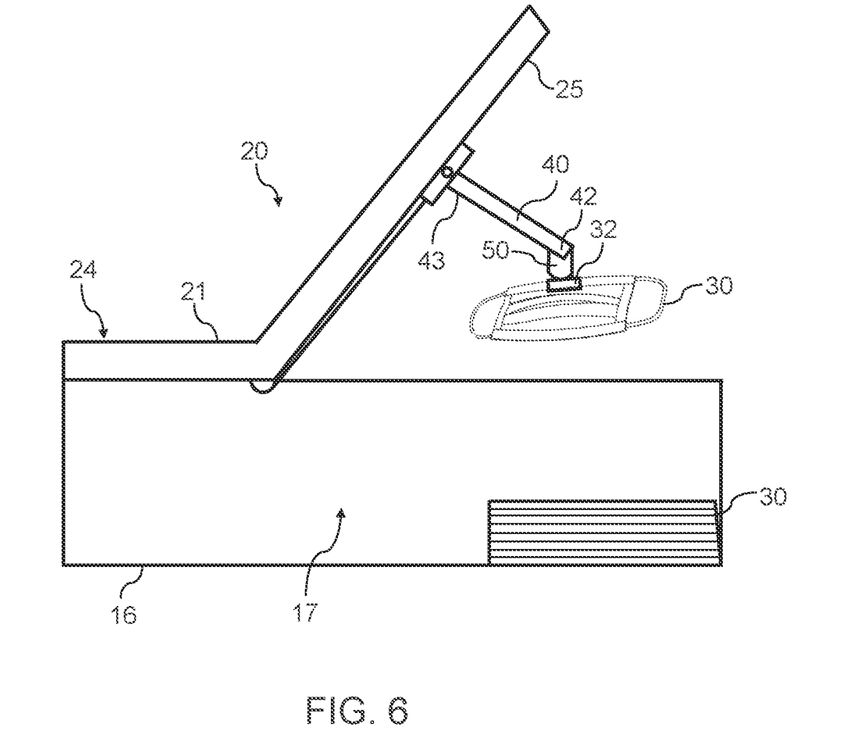
FIG. 6 illustrates a cross sectional view of a dispenser according to example embodiments of the present disclosure.

Now referring to FIGS. 5-6, the cover assembly 20 includes an arm 40 disposed on the inner surface 25. The arm includes a first end 42 and a second end 43. A magnetic device 50 is disposed on the first end 42 of the arm 40. The arm 40 is generally configured such that the magnetic device 50 is configured to engage the metal strip 32 on the facemask 30. For example, as the cover assembly 20 is moved to a closed position the arm 40 is lowered onto the stack of facemasks 30 and the magnetic device 50 can be moved to a position where sufficient contact is established between the magnetic device 50 and the metal strip 32 of the facemask 30. Once sufficient contact is established between the magnetic device 50 and the metal strip 32 of the facemask 30, the facemask 30 can be moved to a dispensing position as the cover assembly 20 is moved towards an open position. Thus, the arm 40 including the magnetic device 50 is configured to lift one or more facemasks 30 from a stored position (e.g., stored in a stacked arrangement in the interior volume 17) to a dispensing position located above the stacked arrangement in order to allow a user to access the facemask 30 in the dispensing position without touching or contaminating facemasks 30 remaining in the stacked arrangement.

Figure 7:
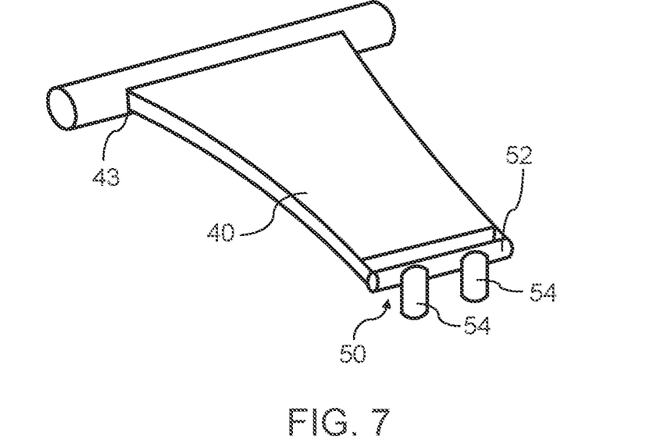
FIG. 7 illustrates a perspective view of an arm for use with the dispenser according to example embodiments of the present disclosure.
Figure 8:
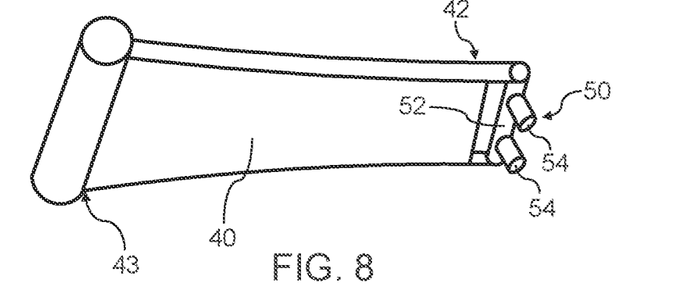
FIG. 8 illustrates a perspective view of an arm for use with the dispenser according to example embodiments of the present disclosure.
Figure 9:
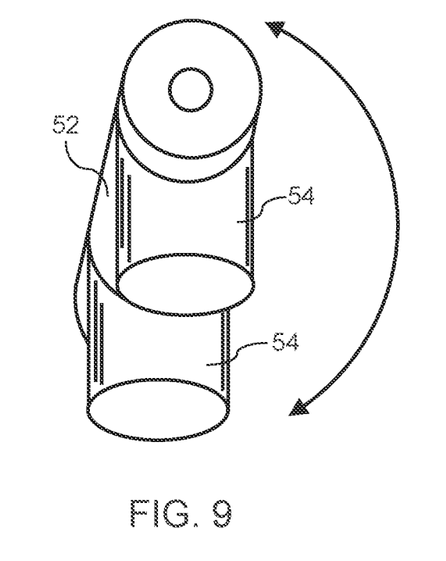
FIG. 9 illustrates a perspective view of a magnetic device for an arm for use with the dispenser according to example embodiments of the present disclosure.

The magnetic device 50 can be coupled to the first end 42 of the arm 40 such that the magnetic device 50 can remain perpendicular to the facemasks 30 as one or more facemasks are removed from the dispenser 10. For example, as shown in FIGS. 7-9, the magnetic device 50 can include a platform 52 pivotally attached to the first end 42 of the arm 40. Pivotal attachment of the platform 52 ensures that the magnets disposed thereon are capable of remaining perpendicular to the stack of facemasks 30 as the angle of attack changes given the removal of facemasks from the stack. Stated differently, pivotal attachment of the platform 52 ensures that the magnets 54 disposed thereon are able to remain flat with respect to a top plane of the facemasks in the stack, such that suitable contact between the magnets 54 and the metal strip 32 can be achieved. Accordingly, pivotal attachment of the platform 52 allows for the attack angle of the magnets 54 to change based on the depth of the facemasks 30 present in the dispenser. For example, as facemasks 30 are depleted from the dispenser 10, the arm 40 tracks lower in order to access the remaining facemasks 30. Accordingly, the platform 52 is configured to pivot such that as the arm 40 tracks lower, the magnets 54 can remain flat against the top of the stacked facemasks 30. The platform 52 can be pivotally attached to the arm 40 via any suitable mechanism. For example, in certain embodiments a pin can be used to pivotally attached the platform 52 to the arm 40.

The magnetic device 50 includes one or more magnets 54, such as rare earth magnets. Rare earth magnets include magnets made from alloys of rare-earth elements. Certain suitable rare earth magnets can include neodymium magnets. Neodymium magnets include those made of an alloy of neodymium, iron, and boron and include those having a chemical formula of $Nd_2Fe_{14}B$. Certain suitable rare earth magnets can also include samarium-cobalt magnets. Samarium-cobalt magnets include those made of alloys of samarium and cobalt including those having a chemical formula $SmCo_5$. Additionally and/or alternatively, other types of magnets can be utilized including magnets made from ferromagnetic materials, such as iron, steel, nickel, cobalt, etc. If rare earth magnets are utilized, they can be coated with any suitable coating. For example, in certain embodiments, the rare earth magnets are coated with a protective coating to reduce the incidence of breakage or damage to the rare earth magnets. In other embodiments, the rare earth magnets can be coated with a plastic coating. The plastic coating can provide further protection to the rare earth magnets from cleaning chemicals. For example, in order to clean the dispenser a variety of antimicrobial and/or sanitizing agents can be used. Use of such agents can lead to corrosion of the magnetic material. Thus, in order to prevent corrosion of the magnetic material, the magnets can be coated such that they can be cleaned with suitable sanitizing agents.

In certain embodiments different types of magnetic devices 50 can be provided and can be interchanged about the first end 42 of the arm 40. For example, different magnetic devices 50 can be provided having different types of magnets that are suitable for lifting different types of metal materials. For instance, stronger or weaker magnets can be included in the magnetic device depending on the type of metal material provided in the metal strip 32 of the facemask 30. Additionally and/or alternatively, magnetic devices 50 can be provided that can pick up (e.g., lift) one or more, such as two facemasks, such as three facemasks, such as four facemasks, etc. from the dispenser. In such embodiments, the magnetic device 50 is configured to dispense more than one facemask at a time. Accordingly, depending on the type of facemask dispensed and/or the metal material used in the metal strip, one or more magnetic devices that are fully interchangeable with the arm can be provided so that the user can adjust the dispenser according to their preferences.

Figure 10:
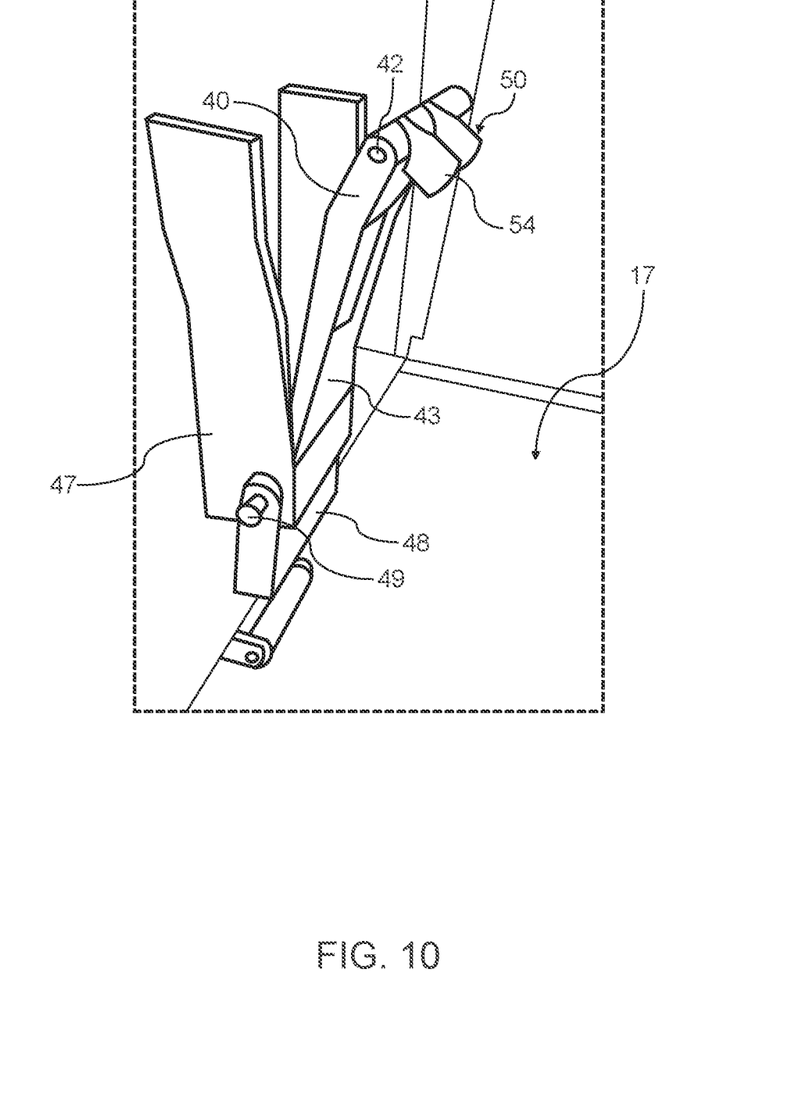
FIG. 10 illustrates a perspective view of an arm coupled to the inner surface of a cover assembly for use with a dispenser according to example embodiments of the present disclosure.
Figure 11:
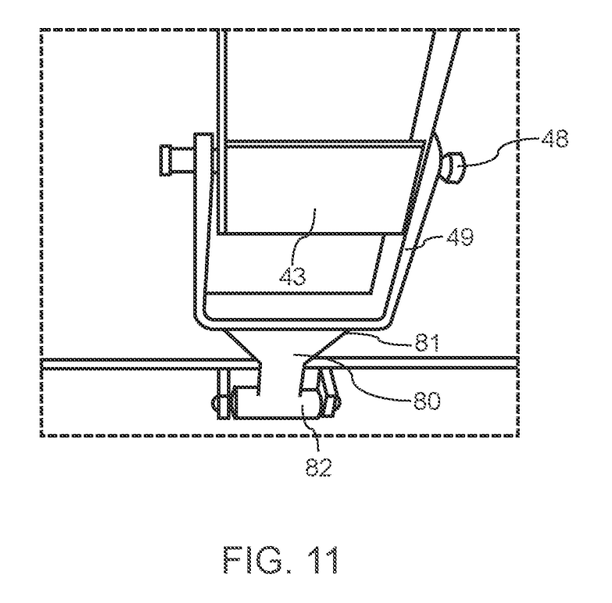
FIG. 11 illustrates a perspective view of a portion of an arm coupled to the inner surface of a cover assembly for use with a dispenser according to example embodiments of the present disclosure.
Figure 12:
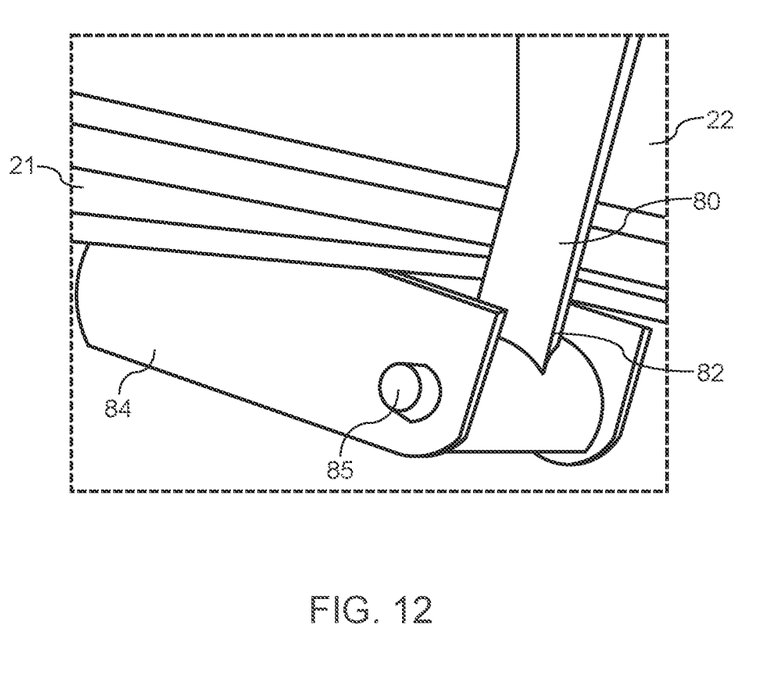
FIG. 12 illustrates a perspective view of a portion of an arm coupled to the inner surface of a cover assembly for use with a dispenser according to example embodiments of the present disclosure.

Additional structural members or other features can be utilized to couple and/or secure the arm 40 about the inner surface 25 of the cover assembly 20. Now referring to FIGS. 10-12, one or more structural members 47, such as a bracket can be used to further secure the arm 40 to the inner surface 25 of the cover assembly 20. For example, disposition of one or more magnets 54 about the first end 42 of the arm 40 can add weight to the first end of the arm 40. Thus, in order to ensure that the arm 40 does not break at or below its pivot point additional structural members 47 can be added to the inner surface 25 of the cover to ensure that the arm 40, including the magnetic device, is securely coupled to the cover assembly 20. As shown, the second end 43 of the arm 40 is pivotally coupled to the inner surface 25 of the dispenser 10. As shown, a pin 48 and bracket 49 can be used to securely mount the second end 43 of the arm 40 in a pivoting manner about the inner surface 25 of the dispenser. Further, an additional support flange 80 extends generally from the second end 43 of the arm and/or the bracket 49. The support flange 80 includes a first end 81 generally coupled to either the second end 43 or the bracket 49 and a second end 82 the is coupled to a bracket 84 secured on the inner surface 25 on the back portion 21 of the cover assembly 20. As noted, the back portion 21 of the cover assembly 20 remains coupled with the housing 16 during operation of the dispenser 10. Accordingly, the bracket 84 provides additional stability for the arm 40, such that the arm 40 does not break away from the cover assembly 20 during use. As shown more specifically in FIG. 12, the second end 82 can be pivotally coupled to the bracket 84 via one or more pins 85.

Figure 13:
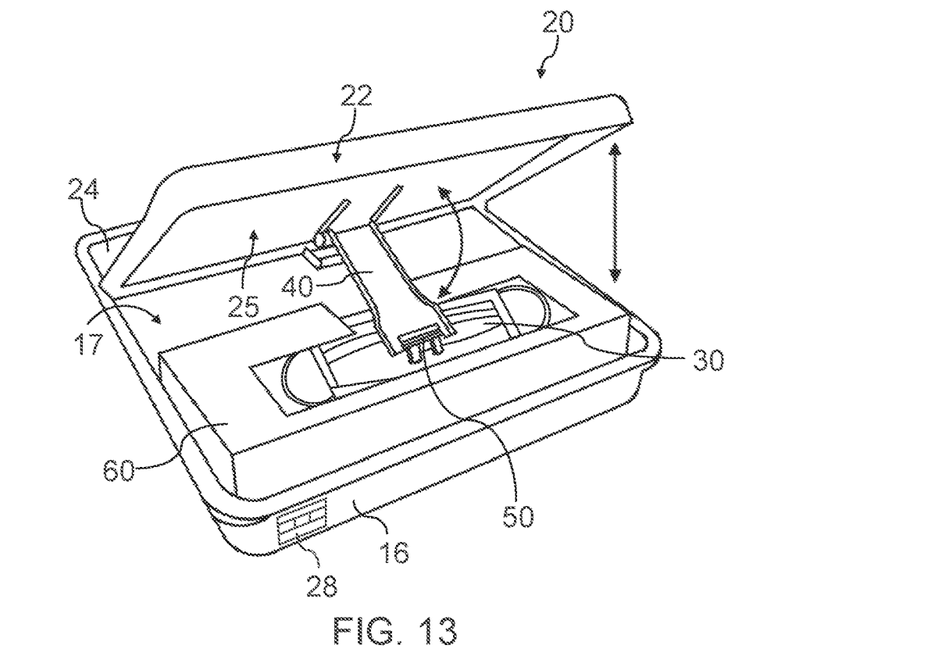
FIG. 13 illustrates a perspective view of a dispenser with the cover assembly in an open position according to example embodiments of the present disclosure.
Figure 14:
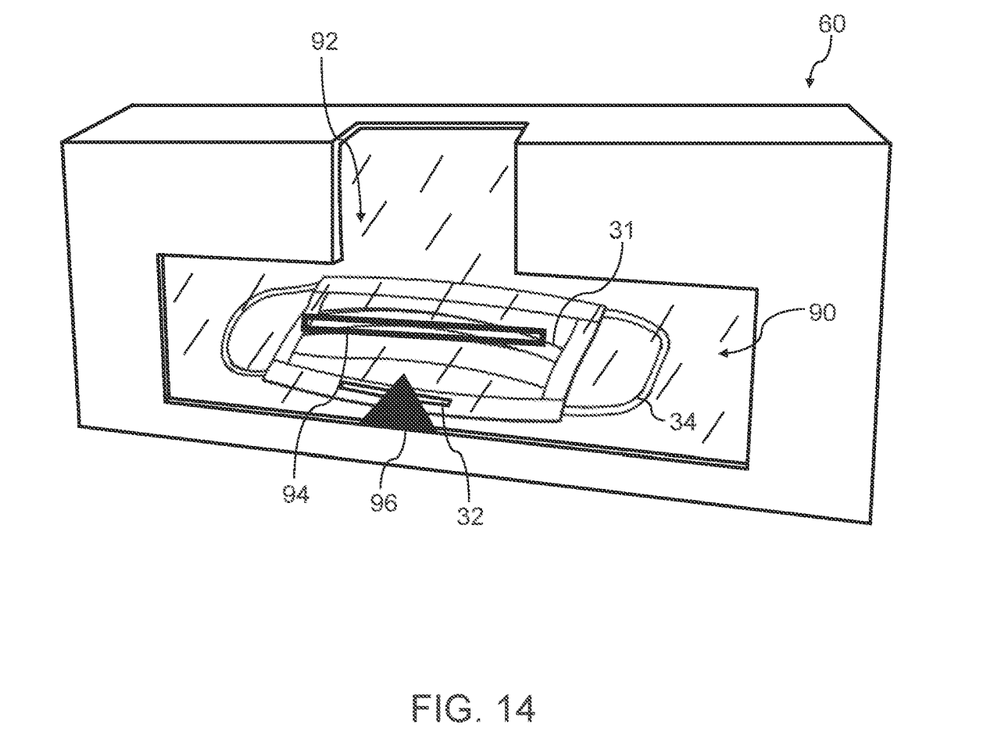
FIG. 14 illustrates a perspective view of an example cartridge for use with a dispenser according to example embodiments of the present disclosure.

Now referring to FIGS. 13-14, in certain embodiments, the dispenser 10 includes a cartridge 60 suitable for holding one or more facemasks 30 in a stacked position. For example, the cartridge 60 can be sized and shaped to fit within the interior volume 17 of the housing 16. Portions of the cartridge, including the top and sides of the cartridge 60 60 can be corrugated such that they can be removed and discarded prior to placement of the cartridge 60 in the interior volume 17. The cartridge 60 can include a paperboard box having one or more perforated section that can be removed and discarded prior to use. Once removed, an opening 90 is formed in the cartridge 60 so that facemasks 30 can be removed therefrom. In certain embodiments, the opening is covered by a thin, plastic film 92, such as a hygienic film. The plastic film 92 ensures that contaminants from the ambient environment are not exposed to the facemasks 30 while they are in a stacked arrangement within the cartridge 60. The film 92 can have one or more slits 94 therein. The slits permit extraction of the facemask 30 from the cartridge. Additionally, one or more control means 96 are provided and are configured to prevent two facemasks 30 from dispensing at the same time should two or more facemasks 30 become entangled in the cartridge 60.

Additional sensors and/or operational components can be included on the dispenser as needed. For example, as shown in FIGS. 1-3 and 13, a variety of sensors 28 can be outfitted on the dispenser 10 and can provide numerous functions. For example, in certain embodiments, the dispenser includes a sensor that is designed to detect the presence of a user in a detection zone. Such sensors are known, and are used to detect when a user is within a certain distance from the product dispenser. In such embodiments, the user detection sensor can be used to open the dispenser such that a facemask can be dispensed from the dispenser upon sensing the user in the detection zone. Again, such sensors are known and can be incorporated into the dispenser 10 provided herein by those of skill in the art. Furthermore, incorporation of a user detection sensor can help further maintain the hygienic state of the dispenser, since the user does not have to touch any portion of the dispenser 10 in order to remove a facemask 30 therefrom. Indeed, as described, when the cover assembly 20 is in a closed position the magnetic device makes contact with the metal strip 32. Therefore, upon the activation sensor sensing a user in the detection zone, the cover assembly 20 can be opened, which allows the arm 40 and magnetic device 50 to move the facemask 30 from a stored position in the stack to a dispensing position that is easily accessible by the user. Additional components, such as controllers, motors, and other mechanical means, can be utilized in order to facilitate opening of the cover assembly 20.

In certain other embodiments, as shown in FIGS. 2-3, the dispenser can include one or more refill detection sensors 29 that can indicate when a low product condition exists. For example, the refill detection sensor can include known components for tracking the amount of product (e.g., facemasks) present in the interior volume of the dispenser. Upon a threshold low product condition being reached, the refill detection sensor can transmit an alert, for example to a user or maintenance personnel, that the dispenser is low on product. For example, when a low product threshold is reached, and externally visible light on the dispenser can be illuminated, indicating that the product is low. For instance, an illuminated red light on an external surface of the dispenser often indicates that a low product condition exists.

Furthermore, the dispenser can include additional components such as a controller, receiver, transmitter, and/or antenna all suitable for receiving and communicating data to and from the dispenser. For example, the controller can include a controller and/or control circuitry configured to control and monitor all the functions of the dispenser including, for example, the amount of product (e.g., facemasks) being dispensed, product usage, and any other activities that are occurring within the dispenser. The control circuitry can be configured to communicate information regarding the dispenser to a server system (e.g., a cloud-based management service) via wired means or through a web-based system as will be described more particularly herein. For instance, the control circuitry can include a receiver configured to interface wirelessly with one or more peripheral devices, including beacon devices. In such embodiments, the dispensers are considered to be "communication-enabled" devices. In certain embodiments, it has been found that Bluetooth Low Energy technology is particularly well-suited for facilitating wireless communication of dispensers 10 in accordance with the present subject matter.

Bluetooth Low Energy devices are well-known to those skilled in the art, and a detailed explanation of their function and operation is not necessary for an understanding and appreciation of the present invention. Briefly, Bluetooth Low Energy beacons are a class of low-energy, low-cost radio transmitters that can alert and/or notify a receiver running Bluetooth Low Energy applications of their presence, which in turn enables the receiver to perform certain actions when in close proximity to the beacon. Each Bluetooth Low Energy beacon broadcasts a unique beacon signal using the Bluetooth Low Energy standard format. These unique signals are also known as beacon "advertisements." The Bluetooth Low Energy receiver runs an application that enables the device to scan for and receive the signals within transmitting range of the Bluetooth Low Energy beacons. The receiver will automatically "react" to the received signal and may start other Bluetooth Low Energy-enabled applications for various purposes, including communication with a central server.

It should be appreciated that the present systems and methods are not limited to Bluetooth Low Energy technology. The beacon device, the receiver, and/or other wireless devices can implement any suitable wireless protocol to perform wireless communications as described herein. As examples, the wireless protocol can include, but is not limited to, Long Range (LoRa), Near Field Communication (NFC), High-Frequency (HF) RFID, Ultra-High Frequency (UHF) RFID, Ultra-wideband (UWB), Institute of Electrical and Electronics Engineers (IEEE) 802.15.4, Thread, Zigbee, Wirepass, Encoean/ISO/IEC 14543.3.1x, WiFi or IEEE 802.11, cellular services (e.g., 4G Long-Term Evolution (LTE), 5G, etc.), NarrowBand-Internet of Things (NB-IoT), or any other suitable wireless protocols. Other communication technologies are also within the scope and spirit of the disclosure.

The dispenser can include any number of operational components housed in the housing and/or located external to the housing. For example, additional driver motors, gear assemblies, and control circuitry, including, for example, controllers or microprocessors, for driving the cover assembly to an open position. Operational components can be mounted directly to the housing or cover assembly or can be part of a module that is received within the housing. For example, the operational components can be part of a module that may be readily removable from the housing for servicing and/or replacing components without the necessity of having to remove the entire dispenser from its support surface. In embodiments where the dispenser includes additional components requiring power, additional battery packs can be included on or within the housing 16 for operating a variety of the components of the dispenser. Further, components of the dispenser can be powered by batteries in a battery component or can be powered by an AC to DC distribution system.

The dispenser and components disclosed herein can be formed from any suitable material including plastic and or metallic materials. For example, in certain embodiments the dispenser and dispenser components can be formed from a plastic material (e.g., polypropylene) including one or more antimicrobial agents. Antimicrobial plastics are known and can be utilized according to the present disclosure. For example, suitable antimicrobial agents are incorporated into thermoplastic material and then can be formed into a variety of antimicrobial plastic components. Suitable antimicrobial agents can include benzoates, propionates, nanosilver. thiabendazole, silver salicylates, silver fluorides, copper carbonates, nanocopper, silver powder, or phosphates. Other known antimicrobial agents can also be utilized in embodiments disclosed herein. Additionally, in certain embodiments, the dispenser and dispenser components can be formed from or coated with metallic materials. For example, the dispenser and related components can be formed from chlorine bleach and/or antimicrobial resistant materials, such as stainless steel. Given the need to maintain the hygienic nature of the dispenser, both the exterior and interior of the dispenser can be cleaned with certain sanitizing agents (e.g., bleach or other known antimicrobials), which can erode certain materials over time. Accordingly, in certain embodiments, it may be desirable to form the dispenser and related components from materials that are resistant to such wear from disinfecting chemicals and chemical preparations.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A dispenser for dispensing a facemask, comprising:
   a housing having an interior volume so as to retain one or more facemasks having a metal strip disposed thereon or therein;
   a cover assembly forming at least a portion of the housing, the cover assembly including an outer surface forming a portion of an exterior of the dispenser and an inner surface facing the interior volume;
   an arm disposed on the inner surface of the cover assembly, the arm including a first end having a magnetic device which is pivotally coupled to the first end of the arm such that the magnetic device remains flat relative to the one or more facemasks as the cover assembly is moved to a closed position, wherein the magnetic device is configured to lift the one or more facemasks to a dispensing position when the cover assembly is moved to an opened position.

2. The dispenser of claim 1, wherein the one or more facemasks comprise a plurality of facemasks disposed in a stacked arrangement.

3. The dispenser of claim 1, wherein the magnetic device includes one or more rare earth magnets.

4. The dispenser of claim 3, wherein the one or more rare earth magnets are coated.

5. The dispenser of claim 1, wherein the one or more facemasks comprise facemasks having one or more pleats thereon.

6. The dispenser of claim 5, wherein the one or more pleats are disposed such that an open end of the one or more pleats faces a front portion of the dispenser.

7. The dispenser of claim 1, wherein the one or more facemasks are rectangular in shape and have one or more ear loops disposed thereon.

8. The dispenser of claim 1, wherein the magnetic device is configured to engage the metal strip on one of the facemasks when the cover assembly is moved to a closed position.

9. The dispenser of claim 1, wherein the arm includes a second end pivotally coupled to the inner surface of the cover assembly.

10. The dispenser of claim 1, wherein the arm is coupled to a structural member about the inner surface of the cover assembly.

11. The dispenser of claim 1, further comprising a cartridge disposed in the interior volume configured to hold the one or more facemasks in a stacked position.

12. The dispenser of claim 11, wherein the cartridge comprises an opening having a film disposed thereon, wherein the film includes a slit through which one or more facemasks can be removed.

13. The dispenser of claim 1, wherein, when in a closed position, the cover assembly fits with the housing in a tongue and groove arrangement.

14. The dispenser of claim 1, wherein the housing and cover assembly are formed from one or more plastic materials.

15. The dispenser of claim 14, wherein the one or more plastic materials comprise an antimicrobial agent.

16. The dispenser of claim 1, comprising an activation sensor capable of opening the cover assembly when a user is located within a certain distance from the dispenser.

17. The dispenser of claim 1, comprising one or more refill detection sensors for indicating when a low product condition exists.

18. The dispenser of claim 1, wherein the cover assembly includes a pivot point such that a back portion of the cover assembly remains coupled to the housing when a front portion of the cover assembly is lifted to an open position.

19. The dispenser of claim 18, wherein the front portion of the cover assembly includes a groove or tab to facilitate opening of the dispenser.

* * * * *